United States Patent [19]

Kanter

[11] Patent Number: 4,487,700
[45] Date of Patent: Dec. 11, 1984

[54] METHOD AND APPARATUS FOR SEPARATING LYMPHOCYTES FROM ANTICOAGULATED BLOOD

[75] Inventor: Robert J. Kanter, Old Bethpage, N.Y.

[73] Assignee: Technicon Instruments Corporation, Tarrytown, N.Y.

[21] Appl. No.: 467,640

[22] Filed: Feb. 18, 1983

[51] Int. Cl.³ .............................................. B01D 21/26
[52] U.S. Cl. ..................................... 210/789; 210/516;
210/927; 435/2; 436/63; 436/177
[58] Field of Search .......................... 210/516–518,
210/359, 789, DIG. 24, 927, 515; 604/6;
436/63, 178, 177; 422/101; 435/294, 29, 30, 2

[56] References Cited

U.S. PATENT DOCUMENTS

| | | | |
|---|---|---|---|
| 3,700,555 | 10/1972 | Widmark et al. | 435/29 |
| 3,709,791 | 1/1973 | Lichtenstein | 435/294 |
| 4,021,340 | 5/1977 | Zine, Jr. | 210/515 |
| 4,190,535 | 2/1980 | Luderer et al. | 210/789 |
| 4,250,041 | 2/1981 | Babson et al. | 210/927 |
| 4,343,793 | 8/1982 | Wissler | 435/2 |

FOREIGN PATENT DOCUMENTS 155891 12/1979 Japan ................................. 210/927

Primary Examiner—Richard V. Fisher
Assistant Examiner—John W. Czaja
Attorney, Agent, or Firm—S. P. Tedesco; C. J. Herron

[57] ABSTRACT

The present invention relates to apparatus and method for separating, by centrifugation, blood lymphocytes from other leukocytes in a blood sample. Small dense particles, either wetted or suspended in a physiological, hydrophilic medium, and a chemically inert hydrophobic barrier material are initially located in a suitable container. When the blood sample is added to the container, the particles are phagocytized by the monocytes and granulocytes, so as to increase their specific gravities. Upon centrifugation, the barrier material, whose specific gravity is only slightly greater than the specific gravity of the lymphocytes and less than the respective specific gravities of the phagocytic cells which have ingested particles and of the erythrocytes (red blood cells) in the blood sample, forms a rigid barrier therebetween, allowing harvesting of the lymphocytes, substantially free of contamination.

20 Claims, 4 Drawing Figures

METHOD AND APPARATUS FOR SEPARATING LYMPHOCYTES FROM ANTICOAGULATED BLOOD

BACKGROUND OF THE INVENTION

1. Field of the Invention

The present invention relates to method and apparatus for separating cellular constituents of a whole blood and, more particularly, for separating by centrifugation peripheral blood lymphocytes to achieve high purity and yield.

2. Description of the Prior Art

The clinical evaluation of biological fluids, such as blood, is a vital part of medical practice. Such evaluation is made in respect of particular constituents of the biological fluid and provides an indication of the medical state of the donor.

Once the blood sample is collected, it is often necessary that the particular constituent of the blood sample to be analyzed is available to the technician in as a pure form as possible. Often, centrifugation is used to separate such constituent. During centrifugation, the blood is "spun-down" in a container for a predetermined time, until all suspended erythrocytes, leukocytes and platelets are separated from the plasma or serum. The serum can be evaluated in respect of clinically significant soluble constituents present therein. Following centriguation, the separated serum and cells (and platelets) are separated, either by decanting, siphoning, or pipetting. The serum can be analyzed, e.g., by automated analytical systems as described in U.S. Pat. No. 4,321,432 which is assigned to the instant assignee, to determine the concentration of selected constituents therein, e.g., glucose, cholesterol, etc. Alternatively, the separated cells and platelets can be evaluated, providing clinically significant information. For example, the absolute and relative number of different kinds of white blood cells (leukocytes) and, also, the platelets are a source of vital information concerning the medical state of the donor. Commonly, separation of leukocytes is achieved by centrifugation, wherein a physiologically inert barrier having a specific gravity between the respective specific gravities of the leukocytes and erythrocytes is initially introduced into a tube containing the blood sample. Accordingly, during centrifugation, the leukocytes, along with the supernatant, and erythrocytes are separated by the barrier. As the respective specific gravities of the different subsets of leukocyctes are similar, the separation of pure lymphocytes, a subset of the leukocytes, is difficult to obtain by this technique. Such technique is described, for example, in U.S. Pat. No. 4,190,535.

As hereinafter employed, purity may be understood to be equal to the number of lymphocytes present in the supernatant after separation divided by the total number of all kinds of leukocytes present in that fraction of blood sample. Yield may be understood to be equal to the total number of lymphocytes of the separated sample divided by the number of lymphocytes in the original whole blood sample. Viability may be understood to be equal to the number of Trypan blue excluding lymphocytes in the separated sample divided by the total number of lymphocytes in such separated sample.

There is a growing need, both in the research and clinical laboratory, for obtaining pure peripheral blood lymphocytes. An evaluation of the lymphocyte population in a blood sample provides information of great clinical significance. For example, in histocompatibility typing, the reaction of lymphocytes to certain reagents (antigens) is useful in determining whether a human organ will be accepted or rejected when transplanted. Also, in a immuno-competence testing, lymphocytes are mixed with particular substances (antigens) and the reaction therebetween noted. The degree of reaction provides an indication of the presence of an immunodeficiency disease, of an auto-immune disease, etc., in a patient. However, to obtain a meaningful evaluation, it is essential that the lymphocytes obtained from a blood sample be highly pure, i.e., void of the presence of other subsets of leukocytes, and accurately reflect the total population of lymphocytes in the original blood sample. A high degree of yield and purity is essential for the evaluation to be truly representative of the medical condition of the patient.

Numerous techniques are known in the prior art for separating lymphocytes. For example, in U.S. Pat. No. 3,709,791, assigned to the instant assignee, method and apparatus are described for separating lymphocytes from other cellular constituents in a whole blood sample. As described, the blood sample is mixed with magnetic particles in a disposable syringe and incubated, whereby the particles are phagocytized by monocytes and neutrophils but not by lymphocytes. In effect, the phagocytic leukocytes are "magnetically tagged"; also, a sedimentation agent is introduced into the syringe to promote sedimentation of the erythrocytes. Subsequently, the blood sample, less the sedimented erythrocytes, is forced from the syringe along the conduit which extends through a high-strength, non-uniform magnetic field. Accordingly, the tagged leukocytes and free magnetic particles are retained in the conduit by such magnetic field, allowing collection of the purified lymphocytes.

Also, centrifugation techniques have been used to separate leukocytes. One widely used technique is described, for example, in *Transplantation*, Vol. 22, No. 21, p. 101 (1976). In practicing such technique, a diluted blood sample is layered onto a Ficoll-Hypaque liquid, which is used as a density barrier and has a controlled specific gravity intermediate the respective specific gravities of the mononuclear leukocytes (and also plasma and platelets) and the erythrocytes and many segmented leukocytes. As the Ficoll-Hypaque is an aqueous liquid, the diluted blood sample must be carefully layered onto the surface thereof, so as to prevent mixing therebetween. Again, because the supernatant and cellular constituents are miscible with the Ficoll-Hypaque, separation of the phases following centrifugation must be again carefully effected. Generally, the sample is diluted (1:1 to 1:4), and the yield obtained is relatively low, at least in part, due to subtle effects of dilution. Also, as the respective specific gravities of the subsets of leukocytes are similar, the purity of separated lymphocytes is low.

Attempts have been made to improve separation of lymphocytes by diluting the sample prior to centrifugation, so as to obtain a somewhat sharper banding of cells at the density barrier/diluted plasma interface. This sharper banding facilitates the harvesting and somewhat increases the lymphocyte yield. However, the yield and purity of the harvested lymphocytes remain at a level which is less than ideal.

Also, advances have been made in respect of density barrier materials useful in centrifugal separation techniques. For example, U.S. Pat. No. 4,021,340 and U.S. Pat. No. 4,333,564 describe the use of hydrophobic gel-like, inert compositions having thixotropic properties. Such materials have certain advantages over Ficoll-Hypaque, in that the introduction of sample into the separating container is facilitated. Because such materials are hydrophobic, there is almost no tendency for the sample, when introduced, to be intermixed with such material. In addition such materials are relatively easily deformed and displaced by centrifugal forces but provide following separation, a relatively undeformable barrier which greatly facilitates separation of the supernatant.

SUMMARY OF THE INVENTION

The present invention is directed to method and apparatus for centrifugally separating lymphocytes in an anticoagulated blood sample, such as to obtain a lymphocyte fraction of high yield and essentially free of contaminating monocytes, neutrophils, and other phagocytic cells (hereafter collectively referred to as phagocytic cells). As is known, the respective specific gravities of the subsets of leukocytes vary little from one to another. For example, monocytes have a range of specific gravity (buoyant density) overlapping that of the lymphocytes and are present in amounts of about 25% of the lymphocyte population. Accordingly, when using conventional centrifugation techniques, the resolution between subclasses or subsets of leukocytes is relatively poor. Hence, the harvesting of only the lymphocyte population is quite difficult.

According to the present invention, the obtainment of a high-yield, high-purity, typically one-step lymphocyte separation is achieved by locating both dense particles, either wetted by or suspended in a physiological, hydrophilic medium, and a hydrophobic inert barrier layer material in a suitable container or tube. Hence, interaction and intermixing between these components, which might trap the dense particles within the barrier material, is positively avoided, such that substantially all particles are available for the phagocytic process. The whole blood sample, which need not be prediluted, is then introduced into the tube and mixed with the particles while being incubated to promote phagocytosis. Following incubation, the tube is centrifuged, whereby the erythrocytes and phagocytic cells, the specific gravities of the latter have been increased by the phagocytic process, pass easily through or around the barrier layer. The resultant supernatant contains platelets and a high yield, high-purity layer of lymphocytes, substantially free of contamination by monocytes or granulocytes. The lymphocytes can then be easily removed, for whatever purpose desired. The entire process requires less than forty minutes, as compared with more than one hour for lymphocyte-separating techniques of the prior art.

Preferably, the barrier material is a water-insoluble (hydrophobic), thixotropic material, which is chemically inert and has a specific gravity slightly greater than that of the lymphocytes to be separated but less than the respective specific gravities of the erythrocytes and phagocytized leukocytes. The barrier material is initially located at the bottom of the container. The particles are coated (wetted with) or suspended in a hydrophilic medium and introduced over the barrier material. Accordingly, there is no tendency for such particles either to adhere to or mix with the barrier material, so as to be unavailable to be phagocytized or to increase the density of the barrier material. Therefore, the tube containing the barrier material and the particles can be stored for a long period, the single requirement being that the hydrophilic material wetting or coating the particles be retained, e.g., by sealing the tube to prevent evaporation.

BRIEF DESCRIPTION OF THE DRAWINGS

The significant advantages of this invention are believed made clear by the following detailed description thereof, taken in conjunction with the accompanying drawings, wherein.

DESCRIPTION OF THE PREFERRED EMBODIMENT

Figure 1:
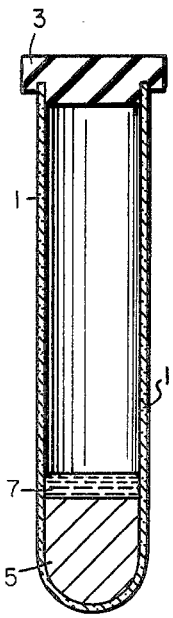
FIG. 1 is a longitudinal-sectional view of the lymphocyte separating apparatus.

Referring to FIG. 1, a container or tube 1, of a type suitable for mounting in a centrifuge, is sealed by rubber stopper 3. Prior to sealing, a gel-like, inert barrier material 5 of controlled specific gravity, i.e., of approximately 1.030–1.087 and a suspension 7 of inert particles, e.g., iron, platinum, gold, silver, lead, etc. or alloys thereof, is placed in tube 1. Such particles have a specific gravity sufficient, when phagocytized, to increase the "effective" specific gravity of the phagocytizing cell in excess of the specific gravity of barrier material 5. For example, the specific gravity of such particles may be greater than about 3.0 gm/cm$^3$. A whole blood sample taken from the patient by direct-hypodermic needle withdrawal, usually with an EDTA anticoagulant, is delivered into tube 1.

Barrier material 5 is selected to be hydrophobic and to either exhibit thixotropic properties or have a melting point at a convenient temperature, e.g., slightly above room temperature, so that it can be centrifuged at room temperature in the liquid state, then cooled slightly below room temperature to solidify to form a relatively firm barrier following centrifuga- tion.

Preferably, barrier material 5 exhibits thixotropic properties and may comprise a mixture of silicone fluid (e.g., a dimethylpolysiloxane) and very fine hydrophobic silica powder. The silicone fluid and the silica particles are mixed together to achieve a gel-like consistency and have an initial viscosity of, at least, about 200,000 cs. Also, the density of barrier material 5 may be set be in the range of about 1.030 to 1.087, which may be controlled by varying the ratio of silicone fluid to silica powder in the mixture. As will be appreciated, the specific density of barrier material 5 would be set, for example, at 1.07 or just greater than the respective densities of the lymphyoctes (and platelets) present in the blood sample, but less than the respective specific densities of the erythocytes and, also, of the monocytes and granulocytes which will have phagocytized the particles.

Alternatively, barrier material 5 may be composed of a mixture of low density liquid, such as n-hexadecane or n-octadecane, etc., and a high denisty halocarbon oil (e.g., Series 27/100–700/100, Halocarbon Products Corp., Hackensack, N. J.), yielding a density between 1.030–1.087 and a melting temperature only slightly below room temperature.

In either case, the amount of barrier material 5 should be sufficient to form a continuous barrier layer transverse to the axis of tube 1 following centrifugation, as shown. For example, and depending upon the dimensions of tube 1, such amount may range between 1.7 and 2.0 grams.

As particular subsets of leukocytes, save for lymphocytes, are phagocytic in nature, the cells of such subsets can be made to attach to foreign substances with which they come into contact, adhering through leukoadhesion, such that phagocytosis follows. While iron particles are employed in the preferred practice of the invention, because of their high specific density, i.e., about 7.5 $gm/cm^3$, it is apparent that any relatively inert particles having a specific gravity greater than about 3.0 $gm/cm^3$ and of a size capable of being ingested by the leukocytes, may be employed. The purpose of such particles is, in effect, to "tag" phagocytic cells and thereby increase their respective "effective" specific gravities in excess of that of barrier material 5. Accordingly, the differential in the respective specific gravities of phagocytic and non-phagocytic leukocytes is very substantially increased and separation thereof is facilitated, as hereinafter described. As a result, the yield and purity of the separated lymophcytes are substantially increased. In addition, lymphocyte viability, in the order of 95%, is maintained.

As the phagocytic process requires the presence of free divalent positively charged ions, e.g., calcium or magnesium ions, dissolved salts such as calcium chloride, or magnesium chloride, etc. are included in the suspension 7. When EDTA is used as the anticoagulant, the addition of such ions serve to restore the ionic content of the "EDTA" blood by replacing free ions which have become bound to the EDTA, to provide a proper ionic concentration in suspension 7. In such case, the suspension 7 also includes a suitable substitute physiological anticoagulant, such as heparin, to prevent clotting of the blood sample after the EDTA is neutralized by the added ions. It will be appreciated that, if the original anticoagulant is heparin, the addition of such ions is unnecessary, as the ionic content of the blood sample is substantially unchanged by such anticoagulant. In addition, the particles in suspension 7 are usually sensitized to promote phagocytosis, by means of a sensitizing agent deposited on the surface of the particles. Such sensitizing agent, which may be included in suspension 7, comprises highly positively charged polymer, for example, a basic polyamino acid or polypeptide, in the nature of D, DL, or L form of polylysine, polyarginine, or the like. The positive charge on the particles tends to substantially enchance the phagocytic process. A better understanding of the phagocytic process may be had by reference to U.S. Pat. No. 3,700,555 and U.S. Pat. No. 3,709,791, which are assigned to the instant assignee.

When barrier material 5 and suspension 7 have been placed in tube 1, rubber stopper 3 is positioned. The prepared tube 1 is available to the technician in the form illustrated in FIG. 1. Inasmuch as the particles are contained in an aqueous medium, so as to be wetted thereby, there is no possibility that significant numbers of such particles would adhere strongly to barrier material 5 or to the wall of tube 1. Accordingly, virtually the entire population of particles in suspension 7 are available for the phagocytic process. Such non-adhesion is insured, because of the hydrophobic nature of the barrier material 5 or of the effective hydrophilic nature of the particles.

Figure 2:
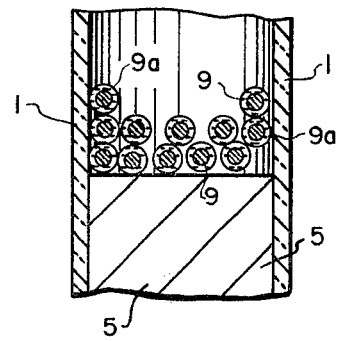
FIG. 2 is a partial longitudinal-sectional view of an alternate embodiment of the lymphocyte separating apparatus.

FIG. 2 shows an alternate embodiment of the invention, wherein the particles are not contained in a suspension. The small number and large size of particles 9, as drawn, are for purposes of illustration only. Rather, such particles, identified as 9, are "wetted" or coated with a very thin layer of hydrophilic material 9a, e.g., an agarose or polyacrylamide coating. Hence, particles 9 tend not to adhere strongly either to the surface of barrier material 5 or of the inside wall of tube 1. Accordingly, when a blood sample is introduced into tube 1, particles 9 are readily suspended in the sample liquid, so as to enter into the phagocytic process. Alternatively, the "wetted" particles 9 could be added concurrently with or subsequent to the addition of the sample into tube 1.

Figure 3:
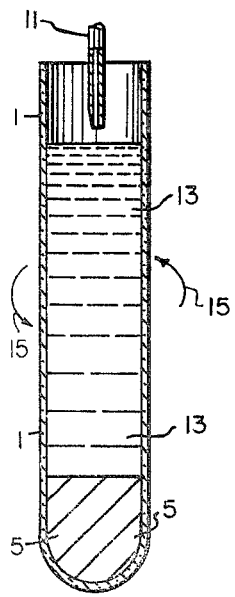
FIG. 3 illustrates the apparatus of FIG. 1, following addition of the blood sample and during mixing and incubation cycles.

Referring now to FIG. 3, the stopper 3 is removed and a given volume of blood sample is introduced into tube 1 via needle 11. If desired, the sample may be introduced by needle 11 directly through stopper 3. In such event, the stoppered tube 1 might be evacuated, to allow for such introduction. Following introduction, tube 1 is re-stoppered and the blood sample and suspension 7 in tube 1, identified as 13, are thoroughly mixed, e.g., in a rotary mixer which is symbolically illustrated by arrows 15. During mixing, mixture 13 is incubated, e.g., at 37° C. for 15–30 minutes. The mixing and incubation are continued for a time sufficient to insure that each of the phago. cytic cells in mixture 13 comes into contact with many particles, to insure phagocytosis. Also, as the particles are, in effect, hydrophilic, essentially all such particles remain available during the mixing process, thereby reducing the total time required for phagocytosis. Accordingly, by either suspending such particles in a "wetting" aqueous medium or by coating the same with a moist hydrophilic material, such particles may be contained in tube 1 for an indefinite period of time and, yet, be immediately available for mixing with a blood sample.

Figure 4:
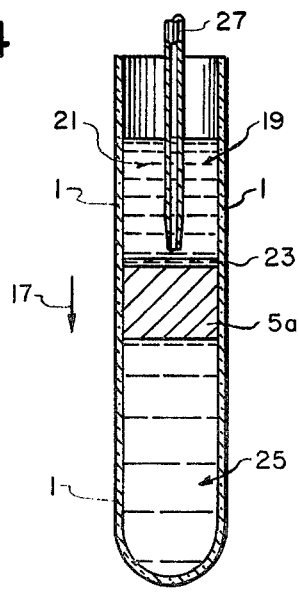
FIG. 4 illustrates the apparatus of FIG. 3, following centri- fugation.

When the phagocytic process has been completed, tube 1 is placed in a centifruge for "spinning-down", as symbolically illustrated by arrows 17 in FIG. 4. During centrifugation, container 1 is rotated at relatively high speeds, e.g., about 1,200×g. Accordingly, the erythrocytes and cells containing phagocytized particles, being of a "high" specific gravity migrate toward the bottom of tube 1, while the lighter platelets and lymphocytes, whose specific gravities have not been modified, move upwardly in container 1. As centrifugation continues, there will be a changing specific gravity gradient of the cellular constituents of the blood sample and the barrier material, each defining a stratum determined by its respective specific gravity. Barrier material 5 will flow under stress and migrate within tube 1, to define a stationary barrier 5a, as illustrated in FIG. 4, which effectively separates the low-density and high-density phases 19 and 25. The low-density phase 19 contains a layer 21 of plasma (and platelets) and a layer 23 of lymphocytes immediately over barrier 5a. The high-density phase or layer 25 includes all other components of the sample, i.e., erythrocytes, leukocytes with phagocytized particles, and all non-phagocytized particles.

As barrier 5a is immiscible with the constituents of lowdensity phase 19 and after cessation of centrifugatal stress is again gelled, the harvesting of the separated lymphocytes is very much facilitated. Since barrier layer 5a is stiff and relatively undeformable following centrifugation, the low density phase 19 can be pipetted up and down by pipette 27 to comingle plasma layer 21 and lymphocyte layer 23, to resuspend the lymphocyte layer 23 without disturbing barrier 5a. Thereafter, the resuspended lymphocytes are removed by pipetting for whatever analytical procedures desired. Alternatively, the greater portion of plasma layer 21 can be initially pipetted off and any remaining portion of layer 21 and lymphocyte layer 23 harvested and transported to another container, for whatever purposes desired.

If barrier layer 5 is formed of a mixture of low and high density materials having a melting point slightly above room temperature, as described above, tube 1 would be cooled sufficiently to solidify barrier 5a and facilitate harvesting of the lymphocytes in layer 23, as described.

While particular embodiments of the invention have been described, it will be apparent that numerous variations may be made without departing from the scope of the appended claims.

What is claimed is:

1. A method for separating lymphocytes from other leukocytes in an anticoagulated blood samples, comprising:
    introducing a hydrophobic, chemically inert barrier material into an open-ended container, so as to be located at the bottom of said container;
    introducing phagocytizable inert particles into said container over said barrier material, said barrier material having a specific gravity greater than said lymphocytes but less than the specific gravity of said particles and of erythrocytes in said blood sample;
    wetting said particles with a hydrophilic material, such that said particles remain over and do not intermix with said barrier material;
    introducing said blood sample into said container to mix with said particles;
    incubating said mixture, whereby at least a portion of said particles are phagocytized by phagocytic leukocytes in said sample;
    centrifuging said container to cause said barrier layer to migrate between said lymphocytes and said leukocytes containing phagocytized particles, unphagocytized particles, and erythrocytes in said sample; and
    harvesting said lymphocytes following centrifugation of said container.

2. The method of claim 1, wherein said wetting step comprises forming a suspension of said particles in a physiological hydrophilic medium.

3. The method of claim 1, wherein said wetting step comprises the step of coating said particles with a hydrophilic material.

4. The method of claim 1, comprising the further step of cooling so as to solidify said barrier material following said centrifuging step.

5. The method of claim 1 comprising the further step of rotating said container to mix said sample and said particles, said rotating step and said incubating step being performed concurrently.

6. The method of claim 5, wherein said rotating step and incubating step are conducted at 37° C. for approximately 15 to 30 minutes.

7. A self-contained unitary separator assembly for the centrifugal separation of lymphocytes from other leukocytes in an anticoagulated blood sample comprising:
    a container having an open end for receiving a blood sample, when introduced into said container and a closed end;
    a hydrophobic, chemically inert barrier material located at said closed of said container;
    inert particles wetted with a hydrophilic material and located over said barrier material, said particles being of a size so as to be phagocytizable by phagocytic leukocytes in said sample; and
    said barrier material having a specific gravity greater than said lymphocytes but less than the specific gravity of said particles and erythrocytes in said sample, such that said particles remain over and do not intermix with said barrier material until subjected to centrifugation.

8. The assembly of claim 7, wherein said barrier material is of a volume sufficient to form a barrier layer between different density phases of said sample following centrifugation of said container.

9. The assembly of claim 7, wherein said barrier material is liquid which becomes solid on cooling slightly below room temperature.

10. The assembly of claim 7, wherein said barrier material has a density of between approximately 1.030 and 1.087.

11. The assembly of claim 7, further including a stopper for sealing said open end.

12. The assembly of claim 11, wherein said container is evacuated.

13. The assembly of claim 7, wherein said inert particles are contained in a physiological hydrophilic medium.

14. The assembly of claim 13, wherein a positively charged polymer is included in said physiological medium as a sensitizing agent to promote phagocytosis.

15. The assembly of claim 14, wherein said medium includes heparin and divalent positively charged ions.

16. The assembly of claim 7, wherein said particles are coated with a hydrophilic material.

17. The assembly of claim 7, wherein said hydrophilic material is agarose or a polyacrylamide.

18. The assembly of claim 7, wherein said particles have a specific gravity greater than approximately 3.0 gm/cm$^3$.

19. The assembly of claim 7, wherein said barrier material has an initial viscosity of, at least, about 200,000 cs and exhibits thixotropic properties.

20. The assembly of claim 7, wherein said particles are formed of a material selected from the group consisting of iron, platinum, gold, silver, lead and alloys thereof.

* * * * *